United States Patent [19]
Horiguchi et al.

[11] Patent Number: 5,538,519
[45] Date of Patent: Jul. 23, 1996

[54] PRODUCTION OF COLORED SILK FILAMENT

[75] Inventors: Shojiro Horiguchi, Omiya; Takae Ogiwara, Akabori-machi; Yoshio Abe, Iwatsuki; Akira Hoshino, Koshigaya, all of Japan

[73] Assignees: Dainichiseika Color & Chemicals Mfg. Co., Ltd., Tokyo, Japan; Shigeji Ogiwari, Gunma-ken, Japan

[21] Appl. No.: 318,256

[22] Filed: Oct. 5, 1994

[51] Int. Cl.$^6$ ............................. D01B 7/00; C09B 69/10
[52] U.S. Cl. ............................. 8/647; 8/538; 8/917
[58] Field of Search ............................. 8/647, 917, 538

[56] References Cited

U.S. PATENT DOCUMENTS 4,000,118  12/1976  Dawson et al. ............................. 8/649 X
4,763,371  8/1988  Parton ............................. 8/647

FOREIGN PATENT DOCUMENTS 54-30944  10/1979  Japan.
3-193904  8/1991  Japan.

Primary Examiner—Margaret Einsmann
Attorney, Agent, or Firm—Oblon, Spivak, McClelland, Maier & Neustadt

[57] ABSTRACT

Described is a method for producing a colored silk filament by having a colorant solution absorbed through the spiracles of each silkworm larva and then allowing the larva to secrete the colored silk filament through the spinneret thereof. In this method, a solution of a polymer-linked dyestuff is employed as the colorant solution.

4 Claims, No Drawings

PRODUCTION OF COLORED SILK FILAMENT

BACKGROUND OF THE INVENTION

1. Field of the Invention

This invention relates to a method for producing a colored silk filament by making each silkworm larvae secrete the colored silk filament. More specifically, this invention relates to a method for producing a colored silk filament having excellent color fastness to light, washing and the like.

2. Description of the Related Art

As a typical illustrative dyeing method of silk, the following method is known conventionally.

First, a dyestuff is dissolved in a small amount of boiling water and the resulting dyestuff solution is diluted to a weight about 50 times as much as the weight of silk to be dyed. Sodium sulfate is then added, whereby a dyestuff solution is prepared. Placed next in the solution is silk which has been washed with hot water in advance, followed by gradual heating so that the solution boils in about 30 minutes. The solution is allowed to stand for about 30 minutes to achieve complete adhesion of the dyestuff onto the silk. After the complete adhesion of the dyestuff on the silk, the silk is taken out from the solution, followed by washing with water and drying, whereby colored silk is obtained.

Instead of dyeing cocoons after their formation, it has been attempted to obtain a cocoon which has already been dyed at the time of its formation.

As disclosed, for example, in Japanese Patent Publication No. SHO 54-30944, it is also known to coat with a dyestuff solution the spiracles of each grown larva, which is of from the fourth diapause to the fifth instar, several times so that the dyestuff is adsorbed on the silk glands within the larva. The larva is then allowed to secrete a silk filament from the spinneret thereof, whereby a colored cocoon is produced.

Alternatively, it is also known, as disclosed in Japanese Patent Laid-Open No. HEI 3-193904, to produce a colored cocoon by dipping each silkworm larva in a dyestuff solution to have the dyestuff adsorbed on its silk gland through its spiracles and then allowing the larva to secrete a colored silk filament through the spinnerets.

The former dyeing method in which silk is dipped in a dyestuff solution needs many production steps and in addition, a considerable time and labor are necessary for each production step. Moreover, this method requires the dyestuff solution about 50 times as much in weight as the silk to be dyed. Thus, large-scaled facilities and a large amount of the dyestuff are indispensable for this method.

Another drawback of the former method resides in the difficulty in controlling the temperature and time. Without proper control, crocking from the silk may take place. In addition, the color shade varies delicately depending on the ratio of the dyestuff to water, thereby making it extremely difficult to dye silk in a desired shade.

In the latter method, a colored silk filament is produced by coating the spiracles of each silkworm larva with a dyestuff solution or by dipping the larva in the dyestuff solution so that the solution is adsorbed on the silk glands within the larva, and then allowing the larva to secrete a dyed silk filament through its spinneret to obtain a colored cocoon. The colored cocoon so formed is however accompanied with such a drawback that severe crocking occurs not only when the cocoon is boiled but also when the boiled cocoon is treated or processed to obtain a colored filament. There are still disadvantages that the colored silk filament has inferior color fastness to light, washing and the like owing to the use of the dyestuff and about 30% of larvae die while they are dipped repeatedly in the dyestuff solution.

SUMMARY OF THE INVENTION

An object of the present invention is therefore to provide a colored silk filament having excellent color fastness to light, washing and the like by a simple method without depending on the above prior art.

The above object has been attained by the present invention which will be described hereinafter. Namely, the present invention provides a method for producing a colored silk filament by having a colorant solution absorbed through the spiracles of each silkworm larva and then allowing the larva to secrete the colored silk filament through the spinneret thereof. In this method, a solution of a polymer-linked dyestuff is employed as the colorant solution.

According to the present invention, when each silkworm larva is dipped in an aqueous solution of a polymer-linked dyestuff, the colorant solution can be absorbed easily through the spiracles of the larva, which serve as a respiratory organ, even if a pigment insoluble in water is employed as the colorant. The reason for the easy absorption resides in that the pigment has been dispersed or dissolved in the solution in a molecular form bonded with the polymer. No silkworm larvae are killed by the dipping. Upon metamorphosis into a chrysalis, the larva secretes a filament containing the polymer-linked dyestuff mixed in the solution, thereby forming a cocoon. By spinning the colored cocoons, a colored lustrous filament can be obtained.

. Further, the polymer-linked dyestuff is mixed in a hypha prior to the secretion and hardening of the hypha which has been accumulated within the body of the silkworm larva. The hypha is therefore dyed directly with the polymer-linked dyestuff solution. This results in uniform dyeing of the secreted silk filament. In the present invention, a polymer-linked dyestuff which has excellent color fastness, particularly fastness to light and washing, is employed as a dyestuff so that the silk filament dyed therewith has excellent light fastness and is free from crocking in the subsequent washing step. The silk filament so obtained contains both the dyestuff and the polymer component so that it has advantages such as luster and improved physical properties.

DETAILED DESCRIPTION OF PREFERRED EMBODIMENTS

The present invention will hereinafter be described more specifically by preferred embodiments.

The polymer-linked dyestuff solution useful in the present invention means a solution of a polymer-linked dyestuff in neutral water, an aqueous acidic solution or an aqueous alkaline solution. The concentration of the polymer-linked dyestuff may range preferably from 0.1 to 15 wt. %.

The polymer-linked dyestuff is considered to have such a structure that the dyestuff moiety and the polymer moiety are chemically linked together into a single molecule. For the synthesis of the polymer-linked dyestuff, many methods are known, which varies in the method of introducing the dyestuff into the polymer and in the kind of applicable polymers.

These production methods of the polymer-linked dyestuff can be classified roughly into the following groups according to the manner of reaction.

(1) Methods in which mutually-reactive functional groups are introduced in the dyestuff and the polymer, respectively and are then reacted.

As one example, a dye such as a C-(hydroxyalkyl)- or N-(hydroxyalkyl)-containing anthraquinone, triphenylmethane or azo dyestuff is reacted to a reactive polymer containing carboxylic halide residual groups, acid anhydride residual groups or other reactive groups therein.

As another example, a dyestuff having an amino or phenolic hydroxyl group is reacted to an epoxy-containing reactive polymer.

(2) Methods in which an addition-polymerizable group such as a vinyl group is introduced into to a dyestuff and the resultant dyestuff is then homopolymerized or copolymerized with another addition-polymerizable monomer.

For example, m-aminostyrene is diazotized and then coupled with one of various grounder components to develop a color. The resultant vinyl-containing azo dyestuff is polymerized.

(3) Methods in which an addition-polymerizable group such as a vinyl group is introduced into one of dyestuff-formable raw materials. The resultant compound is homopolymerized or copolymerized with another addition-polymerizable monomer, followed by reaction with the remaining raw material(s) to develop a color.

For example, m-aminostyrene is polymerized to produce an m-aminostyrene polymer. The resultant m-aminostyrene polymer is diazotized, followed by coupling with one of various grounder components to develop a color.

(4) Methods in which a condensation reactive group is introduced into a dyestuff and the resultant dyestuff is subjected to co-condensation with another condensable monomer or precondensate thereof.

For example, an azo dyestuff, anthraquinone dyestuff, phthalocyanine dyestuff or the like, which have one or more reactive halogen-containing group is subjected to condensation with formaldehyde, an aminoplast resin or the like.

(5) Methods in which a condensing group is introduced into one of dyestuff-formable raw materials and after the resulting material is subjected to co-condensation with another condensable monomer or a precondensate thereof, the co-condensate is reacted with remaining dyestuff-formable raw material(s) to develop a color.

For example, a grounder component having one or more reactive groups is condensed with a reactive polymer, followed by coupling with one or more diazo components to develop a color.

(6) Methods in which dyestuff radicals are formed in an addition polymerizable monomer and the addition polymerizable monomer is then polymerized using the radicals as a polymerization initiator.

In the present invention, it is preferred to employ a polymer-linked dyestuff obtained by mixing and polymerizing an addition polymerizable monomer with the diazonium salt of a pigment, the diazonium salt of a dye or the diazonium salt of a pigment or dye intermediate.

The term "the diazonium salt of a pigment" as used herein means, for example, the diazonium salt of a phthalocyanine pigment such as copper phthalocyanine blue or copper phthalocyanine green, of a vat pigment such as anthraquinone, thioindigo, perinone or perylene, of a polycylic pigment such as quinacridone or dioxazine, of a sulfide pigment, or of an azo pigment such as an azo-coupled and azo-condensation pigment.

On the other hand, the term "the diazonium salt of a dye" means, for example, the diazonium salt of a dye such as an azo dye, anthraquinone dye, indigoid dye, sulfide dye or phthalocyanine dye. The term "the diazonium salt of a pigment or dye intermediate" means the diazonium salt of an intermediate for the above-exemplified pigment or dye, for example, one obtained by introducing a diazonium salt into a known intermediate, such as the diazonium salt represented by the following formula (1):

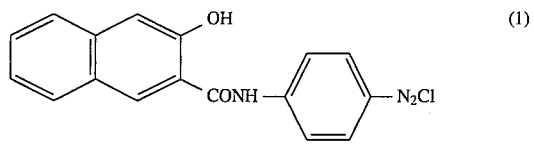

Any known addition-polymerizable monomer can be employed as an addition-polymerizable monomer in the present invention. Examples include vinyl compounds such as acrylonitrile, vinyl acetate, vinyl chloride, vinylidene chloride, styrene, methyl vinyl ketone, methyl vinyl ether, vinylpyrrolidone, vinylpyridine and isobutylene; unsaturated carboxylic acids such as acrylic acid, methacrylic acid, crotonic acid, methylcrotonic acid, itaconic acid, maleic acid, fumaric acid and acetylenedicarboxylic acid, and their derivatives such as esters, acid anhydrides, acid chlorides, acid amides, methylol acid amides and alkyl methylol acid amides; vinyl compounds such as diaminovinyltriazine and vinylurea, and their derivatives such as methylol derivatives and alkylmethylol derivatives; monomers such as glycidyl acrylate, glycidyl methacrylate and acryl glycidyl ether; monomers containing a conjugated double bond such as butadiene, isoprene and chloroprene, monomers containing a non-conjugated double bond, such as ethylene glycol diacrylate, polyethylene glycol diacrylate, diallyl phthalate and N,N'-methylene bisacrylamide; unsaturated polyesters, unsaturated fatty acids, unsaturated fatty acid alkyd resins and drying oils, which contain unsaturated double bonds in their molecules.

With the diazonium salt of the pigment, the diazonium salt of the dye or the diazonium salt of the pigment or dye intermediate, each exemplified above, is mixed with the polymerizable monomer which is also exemplified above and has been selected as desired depending on the application. The resultant mixture is then polymerized by a known method such as solution, emulsion, suspension or bulk polymerization, whereby a colored polymer in which the polymer is chemically-linked with the pigment, dye or intermediate therefor can be obtained.

The present invention will hereinafter be described by Examples. Incidentally, all designations of "part" or "parts" and "%" mean part or parts by weight and wt. % unless otherwise specifically indicated.

EXAMPLE 1

(Preparation of an aqueous solution of a polymer-linked dyestuff)

Four parts (as calculated in terms of a solid content) of a triamino copper phthalocyanine blue hydrochloride paste were mixed with 12 parts of 35% hydrochloric acid, followed by the addition of water and ice, whereby 130 parts of a solution were obtained.

To the resulting solution, 1.2 parts of sodium nitrite were added, followed by diazotization for 20 minutes. After the completion of the diazotization, excess nitric acid was decomposed with sulfamic acid, while observing the progress of the decomposition on potassium iodide starch paper.

The diazonium chloride solution so obtained was filtered and the filtrate was charged into a polymerizer. Fourteen parts of acrylic acid were charged into the polymerizer. The resultant mixture was stirred for 20 minutes at the same temperature, followed by polymerization at 65° C. for 2 hours. The polymerization proceeded with foaming. After the foaming subsided, the polymerization mixture was stirred for further 2 hours. After the polymerization, 200 parts of water were charged into the polymerizer and then, a polymer-linked dyestuff so precipitated was collected by filtration.

The polymer-linked dyestuff so collected was added to and dissolved in a dilute aqueous solution of caustic soda so that the resulting polymer-linked dyestuff solution was adjusted to pH 8 and have a concentration of 5%.

(Production of a colored silk yarn)

In the 5% aqueous polymer-linked dyestuff solution so prepared, plural (about 100) silkworm larvae who had grown up to the fifth instar were dipped for about 2–3 seconds.

The above dipping operation was repeated two to five times. During those operations, any one of the larvae did not die.

According to those operations, the aqueous polymer-linked dyestuff solution was absorbed through their spiracles as respiratory organs, whereby the dyestuff was accumulated in their bodies. No difference was observed between the silkworm larvae with the dyestuff accumulated in their bodies as described above and ordinary silkworm larvae.

After the completion of the above operations the silkworm larvae were sericultured by a usual method. Upon metamorphosis of the larvae into chrysalises, each larva secreted a filament colored with the blue dyestuff, which had been absorbed beforehand in the body, and formed a blue cocoon. By spinning filaments from the cocoons so obtained, a blue silk yarn was successfully obtained. The blue silk yarn so obtained had luster, had physical properties inherent to the copper phthalocyanine blue pigment, was much superior in light fastness to the yarn dyed with a dyestuff, was free from crocking and had excellent light fastness to washing.

EXAMPLE 2

(Preparation of an aqueous solution of a polymer-linked dyestuff)

In a similar manner to Example 1, an aqueous solution of the diazonium chloride of copper phthalocyanine was obtained.

In another reactor, 14 parts of N,N-dimethylaminoethyl methacrylate, 0.6 part of polyethylene glycol nonylphenyl ether and 13 parts of water were charged, followed by stirring to obtain a monomer emulsion. To the emulsion so obtained, the aqueous solution of the diazonium chloride of copper phthalocyanine was added.

Under stirring, 8 parts of a 5% aqueous solution of titanium trichloride were added dropwise to the solution prepared above. Accompanied with the dropwise addition, polymerization proceeded with foaming and the temperature rose to 33° C. by exothermic heat. The end point of foaming was taken as that of the polymerization. After the completion of the polymerization, a polymer-linked dyestuff so precipitated was collected by filtration. Five parts of the polymer-linked dyestuff so obtained were added to 95 parts of a 5% acetic acid solution to dissolve the former in the latter, whereby an aqueous polymer-linked dyestuff solution was obtained.

(Production of a colored silk yarn)

In the 2% aqueous polymer-linked dyestuff solution so prepared, plural (about 100) silkworm larvae who had grown up to the fourth instar were dipped for about 2–3 seconds.

The above dipping operation was repeated two to five times. During those operations, any one of the larvae did not die.

According to those operations, the aqueous polymer-linked dyestuff solution was absorbed through their spiracles as respiratory organs, whereby the dyestuff was accumulated in their bodies. No difference was observed between the silkworm larvae with the dyestuff accumulated in their bodies as described above and ordinary silkworm larvae.

After the completion of the above operations, the silkworm larvae were sericultured by a usual method. Upon metamorphosis of the larvae into chrysalises, each larva secreted a filament dyed in blue with the dyestuff, which had been absorbed beforehand, and formed a blue cocoon.

By spinning filaments from the cocoons so obtained, a blue silk yarn was successfully obtained. The blue silk yarn so obtained had luster, had physical properties inherent to the copper phthalocyanine blue pigment, was much superior in light fastness to the conventional yarn dyed with a dyestuff, was free from crocking and had excellent light fastness to washing.

EXAMPLE 3

(Preparation of an aqueous solution of a polymer-linked dyestuff)

With 6.9 parts of hydrochloric acid and 1.6 parts of sodium nitrite, 4.7 parts of a red chromogen represented by the following formula (2):

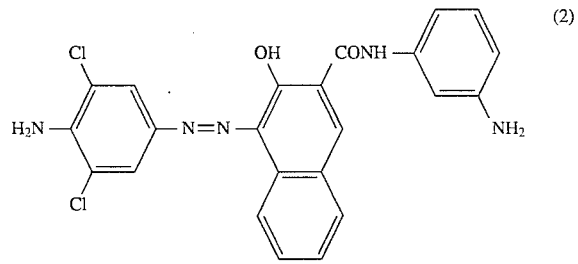

were diazotized. The reaction mixture was filtered. To the filtrate so obtained, a solution of 23.3 parts of acrylic amide in 50 parts of water was added, followed by heating to 65° C. over 30 minutes and then stirring at 65°–70° C. for 30 minutes to conduct polymerization. To the reaction mixture, 150 parts of water were added. The reaction product was then collected by filtration, followed by being washed with methanol and then with water. The paste so obtained was then suspended in 30 parts of water, followed by the addition of 25.2 parts of a 37% aqueous solution of formaldehyde. The resulting suspension was adjusted to pH 9 with sodium carbonate, followed by methylol-forming reaction at 60°–65° C. for one hour. The red solution so obtained was filtered and the filtrate was poured into 200 parts of methanol to precipitate the polymerization product. The precipitate so obtained was collected by filtration. The filtrate was washed again with methanol and then with ethyl ether, followed by drying in air, whereby 27.7 parts of a red polymer-linked dyestuff were obtained.

Five parts of the red polymer-linked dyestuff so obtained were dissolved in 95 parts of water, whereby an aqueous polymer-linked dyestuff solution was obtained.

(Production of a colored silk yarn)

In the 5% aqueous polymer-linked dyestuff solution so prepared, plural (about 100) silkworm larvae who had grown up to the fifth instar were dipped for about 2–3 seconds.

The above dipping operation was repeated two to five times. During those operations, any one of the larvae did not died.

According to those operations, the aqueous polymer-linked dyestuff solution was absorbed through their spiracles as respiratory organs, whereby the dyestuff was accumulated in their bodies. No difference was observed between the silkworm larvae with the dyestuff accumulated in their bodies as described above and ordinary silkworm larvae.

After the completion of the above operations, the silkworm larvae were sericultured by a usual method. Upon metamorphosis of the larvae into chrysalises, each larva secreted a filament dyed in red with the dyestuff, which had been absorbed beforehand, and formed a red cocoon.

By spinning filaments from the cocoons so obtained, a red silk yarn was successfully obtained. The red silk yarn so obtained had luster, had physical properties inherent to the azo pigment, was much superior in light fastness to the conventional yarn dyed with a dyestuff, was free from crocking and had excellent light fastness to washing.

What is claimed is:

1. In a method for producing a colored silk filament by having a colorant solution absorbed through the spiracles of each silkworm larva and then allowing the larva to secrete the colored silk filament through the spinneret thereof, the improvement wherein a solution of a polymer-linked dyestuff is employed as the colorant solution.

2. A method according to claim 1, wherein the solution of the polymer-linked dyestuff has a concentration of 0.1 to 15 wt. %.

3. A method according to claim 1, wherein the polymer-linked dyestuff has been obtained by mixing and polymerizing the diazonium salt of a pigment, a dye or a pigment or dye intermediate with an addition-polymerizable monomer.

4. A method according to claim 1, wherein the solution of the polymer-linked dyestuff is absorbed through the spiracles of each silkworm larva by dipping the silkworm larva in the solution of the polymer-linked dyestuff 2 to 5 times for 2 to 3 seconds each time.

* * * * *